United States Patent [19]

Gyer et al.

[11] Patent Number: 4,472,963
[45] Date of Patent: Sep. 25, 1984

[54] COLD CRANKING SIMULATOR INCLUDING A SAMPLE SUPPLY SYSTEM AND VISCOMETER

[75] Inventors: John F. Gyer, Clarksboro; Donald K. Mosher, Glassboro, both of N.J.

[73] Assignee: Mobil Oil Corporation, New York, N.Y.

[21] Appl. No.: 366,950

[22] Filed: May 24, 1982

[51] Int. Cl.$^3$ .................................. G01N 11/14
[52] U.S. Cl. .................................................. 73/60
[58] Field of Search ................................. 73/60, 59

[56] References Cited

U.S. PATENT DOCUMENTS

| | | | |
|---|---|---|---|
| 2,074,174 | 3/1937 | Goodier | 73/60 |
| 2,812,656 | 11/1957 | Merrill | 73/60 |
| 3,350,922 | 11/1967 | Kim et al. | 73/60 |
| 3,435,666 | 4/1969 | Fann | 73/60 |
| 3,935,726 | 2/1976 | Heinz | 73/60 |
| 4,062,225 | 12/1977 | Murphy, Jr. et al. | 73/60 |

Primary Examiner—Gerald Goldberg
Assistant Examiner—Joseph W. Roskos
Attorney, Agent, or Firm—A. J. McKillop; J. F. Powers, Jr.; M. G. Gilman

[57] ABSTRACT

A cold cranking system for measuring the viscosity of lubricating oils is disclosed. The system includes a viscometer having means for cooling a sample of the oils to a desired temperature for the viscosity measurement. A constant temperature cold bath source is provided for cooling the sample to the desired temperature, where the temperature of the cold bath is controlled to a constant predetermined temperature differential below the desired temperature for the sample. A separate heating bath of hot coolants is also provided to heat the sample after measurement to reduce the sample's viscosity to permit the rapid and complete removal of the sample from the viscometer during introduction of the next sample into the viscometer. A sample supply system is also included for supplying the samples to be measured.

52 Claims, 4 Drawing Figures

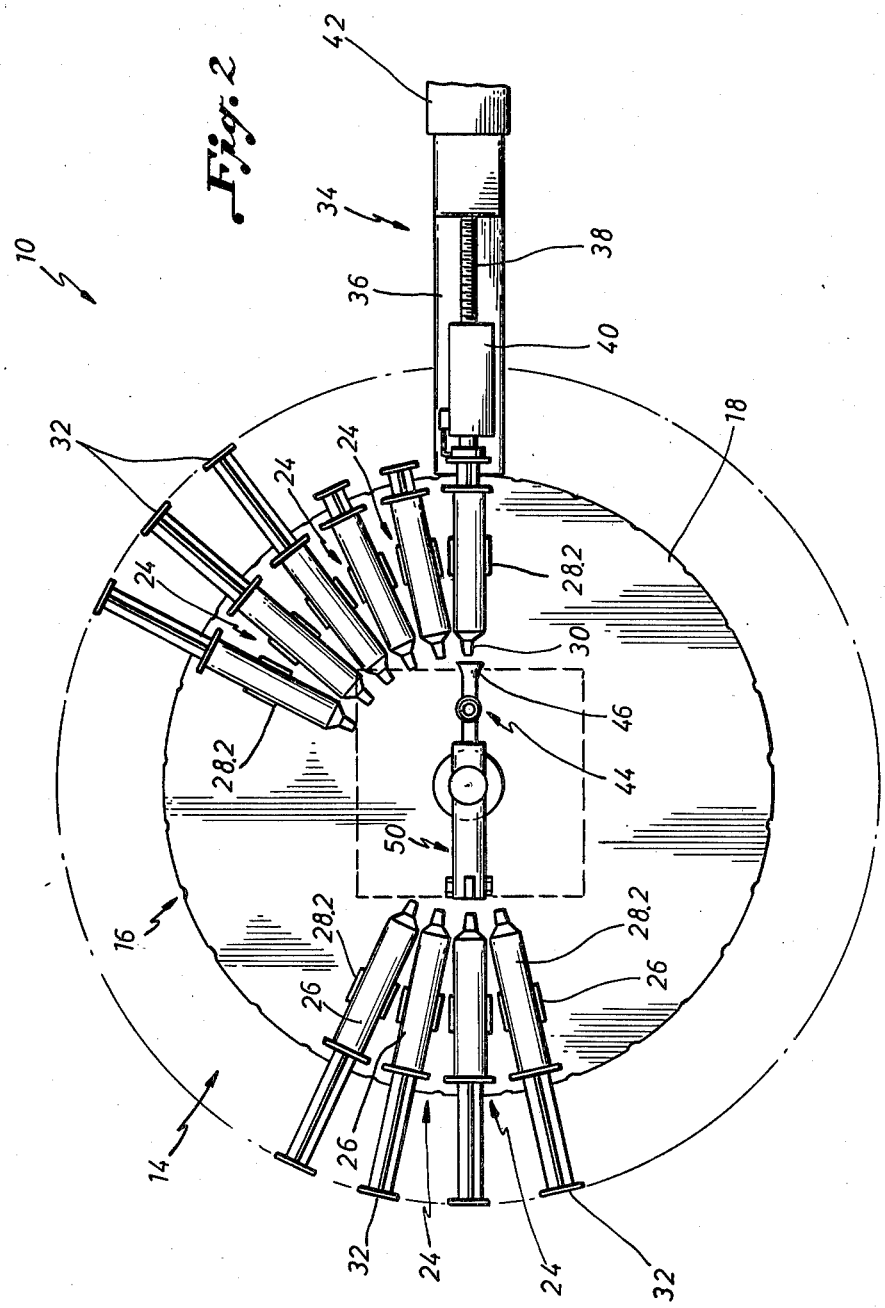

COLD CRANKING SIMULATOR INCLUDING A SAMPLE SUPPLY SYSTEM AND VISCOMETER

Reference is made to co-pending U.S. application Ser. No. 356,585, filed Mar. 9, 1982 which discloses and claims a sample supply system for use in a cold cranking simulator.

This invention relates to viscometers. More particularly, the invention relates to a cold cranking simulator for the automatic measurement of the low temperature high shear stress viscosity of multiple samples of lubricating oils.

According to the American Society for Testing and Materials ASTM standardized test procedure D2602, cold cranking simulators (hereinafter "CCS") are devices which measure the cold temperature viscosity of lubricating oils. In the determination of the viscosity of these lubricating oils, successive samples are placed in a sample chamber where a shear zone containing a portion of the sample is established between the sample chamber and a rotating rotor. Measurements of the rotation of the rotor are taken to determine the oil's viscosity. Prior to the viscosity measurement, the sample is cooled to the desired cold temperature. Usually, the samples are supplied to the sample chamber a sample at a time by means of a pipette or syringe.

Various systems have been employed in the past for the supply of successive samples of fluent samples to be tested or otherwise handled. Many of these systems are relatively clumsy and labor intensive, requiring virtual constant supervision and attendance. Many of these systems are systems in which contamination of succeeding samples by the remnants of preceding samples is difficult to avoid. This is particularly the case where pumps are employed to pump samples selectively into a common manifold, or where large volume suction systems are employed to draw successive samples into a handling zone.

One example of a prior-art CCS is the Cannon Instrument Co.'s Model CCS2. For this system, the oil samples are manually introduced into the sample chamber by an eye-dropper. To cool the samples to the proper temperature, a cold bath of unregulated cold coolant fluid is provided. The temperature of this cold bath is unregulated. The temperature of the bath is related to the temperature for the viscosity measurement only in that the temperature of the bath is colder than the lowest temperature at which a measurement is to be made. The sample chamber contains conduits therein for receiving this coolant fluid.

The desired temperature for the sample is obtained by controlling the passage of this very cold fluid through the sample chamber conduits. Control is obtained by monitoring the temperature of the sample chamber and controllably actuating a solenoid valve in the inlet line to the sample chamber when the temperature is above the desired temperature. The application of the cold coolant fluid into the sample chamber cools the sample chamber much more rapidly than the sample. Control of the solenoid is therefore critical to avoid overshooting the desired temperature for the sample. This problem is compounded by the fact that only the temperature of the sample chamber is being measured and not the sample itself.

After each test, the sample chamber and rotor must be purged and cleaned. In the Cannon CCS, cleaning of the sample chamber begins by isolating the cold coolant fluid contained in a portion of the inlet and outlet lines to the sample chamber and the fluid in the chamber. This isolated fluid is circulated past a heating element and through the sample chamber to raise the temperature of the sample contained in the sample chamber. Further cleaning of the sample chamber must wait a significant amount of time while the isolated coolant fluid is heated.

The sample chamber is then purged and bathed in hot water, whereafter it is washed with naptha and then with acetone. Thereafter it is dried.

Since naptha and acetone are both of relatively low viscosity with respect to oils, solvent residues will introduce errors. In addition, both naptha and acetone create undesirable vapors in laboratory environments.

Thus, it would be advantageous to provide a CCS in which the cold temperature can more accurately reliably and easily be maintained for the various viscosity temperatures and viscosity ranges for the multiple samples to be measured. It would also be advantageous to provide a CCS with a mechanism which reduces the time to heat the measured sample to obtain a low viscosity before purging of the sample chamber. Additionally, it would be advantageous to provide a CCS with the above advantages and also provide an automatic supply system for delivering the samples to be measured where purging and cleaning of the sample chamber can be accomplished through heating of the sample chamber and injection of the next sample to be measured.

In accordance with one aspect of the present invention there is disclosed a viscometer adapted for use in a cold cranking simulator system for measuring the cold cranking viscosity of lubricating oils, the simulator system sequentially measuring the viscosity of a plurality of lubricating oil samples. The viscometer comprises a sample container for receiving a sample to be measured, said container including means separate from the sample for circulating coolant fluids therethrough to control the sample temperature for the viscosity measurement. The container further includes a rotatable rotor contained therein and surrounded by the sample to be measured, said rotor and said sample container defining therebetween a shear zone containing a portion of the sample to be measured.

The viscometer also includes a drive means connected to said rotor for rotating said rotor within said sample container, a measurement means responsive to the rotation of said rotor for measuring the viscosity of the sample, and a source of cooling fluid for cooling the sample in said sample container to the desired temperature for the viscosity measurement. The temperature of the cooling fluid is maintained at a predetermined constant temperature differential below the desired temperature for the sample. Also included is a means independent of said source of cooling fluid for heating said container and sample after each viscosity measurement to decrease the viscosity of the sample oil to enable the rapid and complete replacement of the old sample with a new sample.

The drive means includes a programmable DC current source for supplying a predetermined and constant drive current to a DC motor connected to the rotor. A speed indicator is connected to the motor-rotor combination to indicate the speed that the motor attains in response to the DC current drive. The motor speed obtained represents the viscosity of the sample.

In an alternate embodiment, the DC current source is programmed to supply a drive current sufficient to achieve a predetermined motor-rotor speed. The speed indicator generates a signal representing the speed of rotation of the rotor. The amount of torque required to prevent rotation of the motor stator is measured when the desired rotor speed is obtained. This torque represents the viscosity of the sample. In yet another embodiment, the motor for rotating the rotor is an AC synchronous motor driven from an AC power source.

In a preferred embodiment of the invention, the means for heating the sample chamber and sample after each viscosity measurement comprises a separate source of heating fluid independent of the cooling fluid whereby heating of the measured sample prior to removal from the sample chamber is accomplished by circulation of the heating fluid through said sample chamber in place of the cooling fluid.

In another aspect of the invention, a microprocessor controlled viscometer is provided for measuring the cold cranking viscosity of a sample of lubricating oil contained in a shear zone defined by the space between an outer stationary stator and an inner rotatable rotor, the stator having means therein for receiving fluid coolants separate from the sample. The viscometer comprises a microprocessor programmed to monitor the temperature of each sample and to determine the viscosity of each sample from the speed of rotation of said rotor. Also included is a rotor drive means responsive to said microprocessor for rotating said rotor, a speed indicator responsive to rotation of said rotor, the speed of rotation of said rotor representing the viscosity of the sample, and a supply of cooling fluid responsive to said microprocessor for cooling the sample contained in said stator to the desired temperature at which the viscosity measurement is to be taken. The temperature of the cooling fluid is maaintained at a predetermined constant temperature differential below the desired temperature.

Further included is a supply of heating fluid for heating the sample contained in said stator, and a circulating means responsive to said microprocessor for selectively circulating the cooling and heating fluids through the coolant receiving means in said stator whereby, circulation of the constant temperature cooling fluid lowers the temperature of the sample to the desired temperature for the viscosity measurement, and circulation of the heating fluid heats the sample to obtain a lower viscosity to permit the rapid and complete removal of the sample from the sample chamber.

The means for measuring rotation of said motor comprises an optical incremental shaft encoder. Included in the viscometer of the invention is a temperature probe in the form of a thermister for indicating to the microprocessor the temperature of the stator, i.e., the temperature of the sample.

In yet another aspect of the invention, a CCS is provided for automatically measuring the cold cranking viscosity for each of a plurality of fluent samples, comprising a stator having a sample receiving zone for receiving the sample to be measured, said stator further including means separate from the sample for receiving fluid coolants to control the temperature of the sample, and a temperature probe for generating a signal as a function of the temperature of the stator. A rotatable rotor is contained in said stator and in contact with the sample to be measured, said rotor and said stator defining therebetween a shear zone containing a portion of the sample to be measured.

Also included is a drive means connected to said rotor, said drive means rotating said rotor without rotation of said stator, and a control means for controlling said drive means to rotate said rotor, the resultant speed of rotation of said rotor representative of the viscosity of the sample. The CCS also contains a source of coolant fluid responsive to said control means, said source containing a hot bath of coolant fluid for heating the sample in said sample receiving zone prior to removal of the measured sample and a cold bath of coolant fluid for cooling the sample to the desired temperature at which the viscosity measurement is to be taken. The temperature of said coolant bath is controlled to a constant predetermined temperature differential below the desired temperature for the measurement.

A fluid circulating means responsive to said control means is provided for selectively circulating either the cooling or heating fluid through the coolant receiving means in said sample chamber whereby, circulation of the constant temperature differential cooling fluid controls the temperature of the sample to the desired temperature for the viscosity measurements, and circulation of the heating fluid heats the sample to obtain a lower viscosity to permit the rapid removal of the sample from the sample chamber. A sample supply system responsive to said control means is provided for supplying successive samples of fluent material to the sample receiving zone whereby each sample next to be measured is used to purge the measured sample from the sample receiving zone during loading of the next sample.

In the preferred embodiment of the invention, the sample supply system includes a magazine having a plurality of locating stations for the locating sample receptacles on the magazine, said sample receiving zone receiving samples of fluent material discharged from such sample receptacles, and a discharge member adapted to be actuated to withdraw fluent material from a sample receptacle, the magazine being displaceable relatively to the sample receiving zone and the discharge member to bring any locating station into register with the sample receiving zone and the discharge member for the discharge of fluent material from a receptacle located at such locating station.

The discharge member may be a member of any suitable type for its required purpose, and may be a member actuated by any appropriate means. Thus, for example, the discharge member may produce fluid pressure or mechanical pressure to act on fluent material contained in a sample receptacle.

In an embodiment of the invention, the discharge member may comprise a discharge arm which is adapted to be displaced relatively to a locating station to apply pressure to a fluent material in a receptacle located at such station. The discharge arm may conveniently be adapted to displace a displaceable wall such as a diaphragm or plunger associated with a fluent material receptacle located on a locating station.

In a preferred embodiment of the invention, the discharge member includes a screw assembly to which the discharge arm is connected, with the screw assembly being adapted to be rotatably driven to advance and retract the discharge arm.

The system may preferably include a motor for driving the discharge member and a controller for controlling operation of the motor.

The motor may preferably be in the form of a linear stepping motor, while the controller may be in the form of a computer or a microprocessor which is programmed to operate the motor in a required mode.

The magazine may conveniently be displaceable by being in the form of a rotatable member adapted to be rotatably driven to position the locating stations selectively in register with the discharge member and the sample receiving zone. Alternatively, the magazine may, for example, comprise a displaceable flexible belt, a conveyor or endless belt, a displaceable carriage or rack, or the like.

The magazine preferably has the locating stations arranged in a circumferentially spaced annular arrangement, and preferably has locating means associated with or adapted to be associated with the locating stations for locating sample receptacles on the locating stations. While sample receptacles may be permanently mounted on the rotatable member, they are preferably removably mounted thereon to allow ready replacement of samples, and to allow used sample receptacles to be discharged or cleaned.

The locating means may, for example, comprise an annular locating ring having recesses for accommodating or engaging with sample receptacles. The ring may be displaceable or removable. Alternatively, the locating means may comprise locating members mounted on the magazine at the locating stations.

The system preferably includes a motor for driving the magazine, with the motor being controlled by the controller to bring the locating stations successively into register with the discharge member in a predetermined order.

The sample receiving zone may conveniently comprise a guide tube to guide discharged fluent material from a discharge zone to a handling zone.

In a preferred embodiment of the invention the guide tube has a guide inlet at one end and a guide outlet at its other end, and is displaceable between an operative position where its guide inlet can register with a discharge outlet of a receptacle located at a registering locating station, and an inoperative position where its guide inlet will be spaced from such a receptacle discharge outlet to permit relative movement of the guide tube and the magazine.

The system may include any suitable displacement member for displacing the guide tube between its operative and inoperative conditions. The displacement member may, for example, be in the form of a motor, an air piston, or the like.

The system preferably includes purging means for purging the system between successive samples. The purging means may conveniently be a vacuum or pressure operated purging system which can be selectively actuated to purge the operative portion of the system, or selected portions thereof, during use.

While the sample supply system of this invention may have various applications, it has particular application where a number of successive samples of fluent material must be supplied to a receiving zone of instrument, and where contamination between successive sample is undesirable. The invention therefore has particular application in regard to viscometers, and more specifically in regard to viscometers for use in establishing the viscosity of lubricating oils and the like.

An embodiment of the invention is now described by way of example with reference to the accompanying drawings.

In the drawings:

FIG. 2 shows a diagrammatic, fragmentary, sectional plan view of the system of FIG. 1 along line II—II: except that the system of FIG. 2 has an alternative form of locating means;

Figure 1:
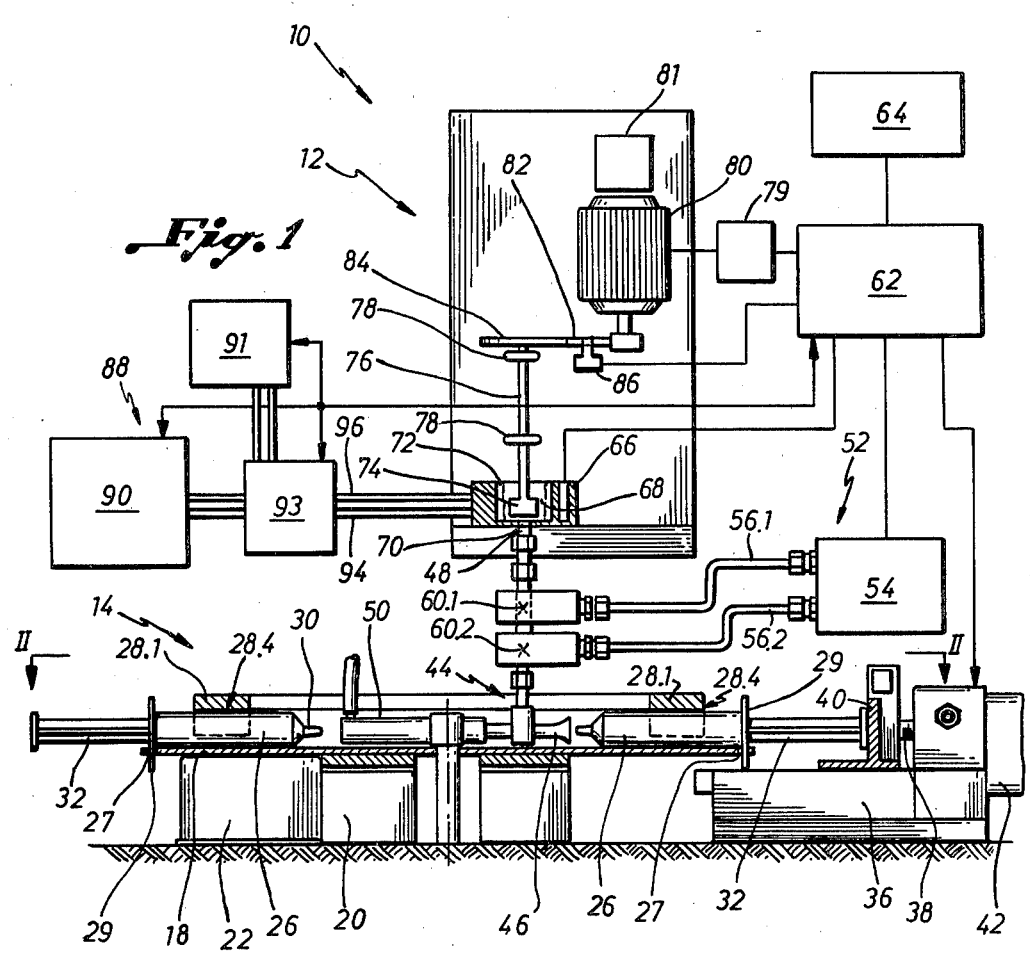
FIG. 1 shows a diagrammatic side elevation of the present invention, including a viscometer system and a sample supply system.

With reference to the drawings, reference numeral 10 refers generally to a CCS in accordance with this invention. The CCS 10 comprises a viscometer 12 for measuring the low temperature high shear stress viscosity of samples and a sample supply system 14 for supplying samples of fluent materials in the form of lubricating oil to viscometer 12 for determination of the viscosity of such samples.

The sample supply system 14 comrises a magazine 16 which is displaceable by being in the form of an annular turntable 18 which is rotatably supported on a base 20. A magazine motor 22 is mounted on the base 20 for rotatably driving the turntable 18. The magazine motor is preferably in the form of a linear stepping motor.

The annular turntable 18 has a plurality of circumferentially spaced locating stations 24 which are arranged in an annular band for supporting a plurality of sample receptacles 26 in appropriate predetermined positions on the turntable 18.

The system 14 includes locating means for locating the sample receptacles 26 at the locating stations. The locating means comprises circumferentially extending slots 27 which are provided in the turntable 18 at each locating station for receiving a flange 29 of each receptacle 26 to thereby locate the receptacles radially on the turntable 18.

The locating means further comprises an annular locating ring 28.1 in FIG. 1. The ring 28.1 has semicircular recesses 28.4 in its downwardly directed surface to receive the receptacles 26 and locate them circumferentially at the locating stations 24. The ring 28.1 further has locator pins (not shown) for engaging with corresponding holes in the turntable to locate the ring 28.1 in its appropriate orientation on the turntable 18. The ring 28.1 may be lifted slightly to allow removal or insertion of receptacles 26.

Each sample receptacle 26 is in the form of a syringe of conventional type, having a discharge outlet 30, and having a displacement plunger 32.

The syringes 26 are preferably in the form of disposable syringes which may be filled with samples of fluent materials to be tested, and may then be discarded after use thereby eliminating the labor costs involved in cleaning sample receptacles, and positively avoiding contamination of succeeding samples by preceding samples.

The sample supply system 14 further comprises a discharge member 34 which is mounted in position and is adapted to be actuated for discharging samples of liquid from the syringes 26 during use.

The discharge member 34 comprises a housing 36 within which a screw assembly 38 is mounted. A displaceable discharge arm 40 is mounted on the screw assembly 38. The screw assembly 38 is adapted to rotatably driven to advance the discharge arm 40 towards the center of the turntable 18, or to retract the discharge arm 40.

The discharge member 34 further includes discharge member drive means in the form of a linear stepping motor 42 for driving the screw assembly 38.

The discharge member 34 is mounted so that the turntable 18 can be rotatably displaced relatively thereto, and so that when any locating station 24 is in register with the discharge member 34, displacement of the discharge arm 40 will cause the discharge arm 40 to engage with a plunger 32 and to advance such plunger 32 for discharging liquid from the syringe 26 located at such locating station 24.

The sample supply system 14 further comprises a sample receiving zone in the form of a guide tube 44 to guide discharged samples of liquids to a handling zone, or sample chamber 66 (see FIG. 3) forming a part of the sample receiving zone. The sample chamber is also part of the viscometer 12.

The guide tube 44 has a guide inlet 46 and a guide outlet 48.

The guide tube 44 is displacable between its inoperative position as shown in the drawings, and an operative position where its guide inlet 46 can register with and engage with a discharge outlet 30 of a syringe 26 which is located on a locating station 24 in register with the discharge member 34 and the guide tube 44.

The sample supply system 14 includes a displacement member 50 for displacing the guide tube 44 between its operative and inoperative positions. The displacement member 50 preferably comprises an air piston of any conventional type which is actuable to displace the guide tube 44 into its operative position, and which can be deactivated for a spring incorporated in the member 50, to return the guide tube 44 to its inoperative position.

The sample supply system 14 further includes purging means 52 for purging the viscometer system 10 between successive samples.

The purging means 52 comprises a vacuum source 54 to provide a purging effect. The purging means 52 further comprises a first purging conduit 56.1 and a second purging conduit 56.2. The first purging conduit 56.1 extends from the vacuum source 54 to one end of a purging section of the guide tube 44 proximate its guide outlet 48, while the second purging conduit 56.2 extends from the vacuum source 54 to an opposed end of the purging section of the guide tube 44 proximate the guide inlet 46.

A first three-way valve 60.1 is provided at the junction of the first purging conduit 56.1 and the guide tube 44, whereas a second three-way valve 60.2 is provided at the junction of the second purging conduit 56.2 and the guide tube 44.

The first and second three-way valves can be operated selectively for purging of the system. Thus, for example, the second three-way valve 60.2 may be closed while the first three-way valve 60.1 may be open to permit purging from the guide tube 44 on the downstream side of the second three-way valve, and at the same time to permit purging from the sample chamber 66 of viscometer 12. Thereafter, the first three-way valve 60.1 may be closed while the second three-way valve 60.2 is opened to permit purging from the upstream side of the guide tube 44 upstream of the first three-way valve.

In an alternative arrangement, the first three-way valve 60.1 may be opened to permit purging from the down-stream side of that valve, and the second three-way valve 60.2 may be opened to permit purging from the upstream side of that valve. Therefore, both parts can be purged at the same time.

The CCS 10 further comprises a control means which incorporates a memory 64 and a controller 62. The controller 62 may be in the form of a computer or a microprocessor of any appropriate type. For the preferred embodiment of the invention, controller 62 is a Commodore CBM 8032 computer. The controller 62 is operatively connected to the motor 42 of the discharge member, to the magazine motor 22, to the air piston of the displacement member 50, and to the vacuum source 54 to thereby effectively and automatically control operation of the sample supply system 14.

The guide outlet 48 of the guide tube 44 is connected to viscometer 12 for supplying samples of lubricating oils contained in the syringes 26 to the viscometer for viscosity determination.

Figure 3:
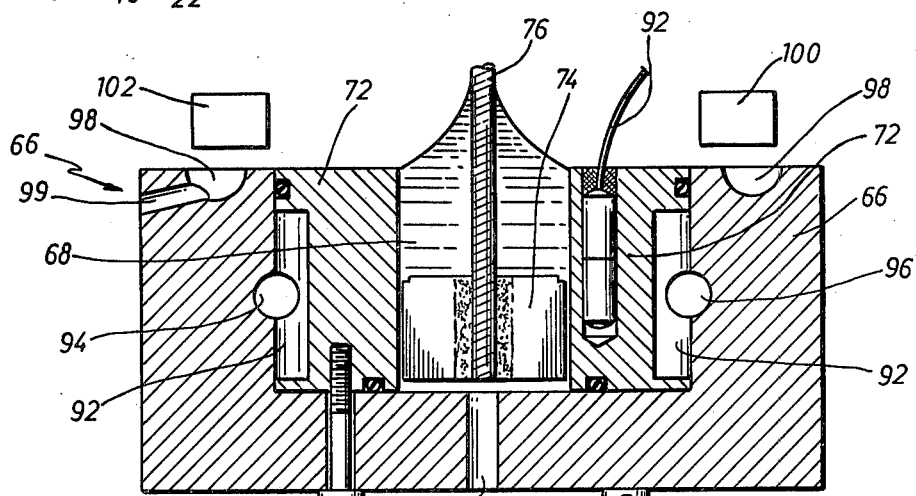
FIG. 3 shows, to an enlarged scale, a cross-sectional side elevation of a portion of the sample receiving zone, i.e., the sample chamber, of the cold cranking simulator of FIGS. 1 and 2.

Referring now to FIGS. 1 and 3, viscometer 12 comprises a sample chamber 66 for receiving samples of fluid for determining the viscosity of such samples. The sample chamber 66 is sometimes referred to as the stator. The stator 66 remains stationary during viscosity measurement obtained as described below.

The sample chamber 66 has a sample cavity 68 where the samples are fed for the viscosity determination, and has an inlet conduit 70 leading to the sample cavity 68. The guide outlet 48 of the guide tube 44 is connected to the inlet conduit 70.

The viscometer 12 further includes an essentially cylindrical rotor 74, having 180° opposed slightly flattened portions, which is rotatably mounted on a shaft 76 which is rotatably supported in bearings 78. These flattened portions of the cylindrical rotor are for hydrodynamic centering of the rotor 74 in the sample chamber. The shaft 76 is flexible below the lower bearing 78. The rotor 74 is contained in the sample cavity 68 such that there is a small clearance between the outer surfaces of the rotor 74 and the inner surfaces of the sample cavity 68. This area defines a shear zone for the fluent sample to be measured.

The viscometer 12 further comprises a variable speed, substantially constant torque electric motor 80 which drives a belt 82. The belt is mounted on a pulley 84 which is mounted on the shaft 76 for the motor 80 to drive the rotor 74.

A speed indicator device 86 is provided in a position to be driven by the belt 82 for giving an indication of the rate of rotation of the rotor 74. The speed indicator could alternately be mounted directly to the rotor shaft 76 for rotation therewith. For the presently preferred embodiment, an optical shaft encoder is used for indicator 86, but a speed tachometer could also be used.

The motor 80 is connected to a programmable DC current source 79 which responds to microprocessor 62 for providing a constant current drive current to motor 80. Also connected to motor 80 is a device 81 for preventing rotation of the motor stator when a viscosity measurement is in progress. Device 81 indicates to the microprocessor 62 the amount of torque required to prevent rotation of the motor 80 stator.

The speed indicator device 86 is likewise connected to the microprocessor 62 so that the microprocessor 62 may determine the viscosity of the liquid from rotation of the rotor 74.

The viscometer 12 also includes a temperature probe 88 (see FIG. 3) for monitoring the temperature of the stator 66. The output from temperature probe 88 is supplied to the microprocessor 62 for processing therein. For the presently preferred embodiment of the invention, the temperature probe 88 is a thermister, but other appropriate devices for monitoring temperature may be used.

Included within the stator 66 is a system of conduits 92 which surrounds the sample chamber 68 but isolated therewith. The conduit 92 includes an inlet conduit 96 and an outlet conduit 94. These conduits are adapted for receiving coolant fluids therethrough for controlling the temperature of the stator 66.

Connected to the inlet conduit 96 and outlet 94 is a circulating means 93 which supplies the coolant fluids for control of the temperature of the stator 66. Circulating means 93 responds to control signals from the microprocessor 62 for selectively applying either a coolant fluid from a cold bath 90 or a heated coolant fluid from a hot bath 91. In the presently preferred embodiment, the coolant fluid for both baths is methanol. Both the coolant fluids from the cold bath 90 and hot bath 91 are maintained at constant temperatures in response to control signals from microprocessor 62.

The temperature of the cold bath 90 coolant fluids is maintained at a constant predetermined temperature differential below the desired temperature for the sample whose viscosity is to be measured, while the temperature of the hot bath 91 coolant fluids is maintained at the maximum temperature possible before boiling of the coolant fluid occurs. The temperature of the hot bath 91 coolant fluids is maintained below the coolant fluid's boiling point in order to avoid the introduction of gas bubbles into the fluid which circulating means 93 circulates through the stator 66.

Figure 4:
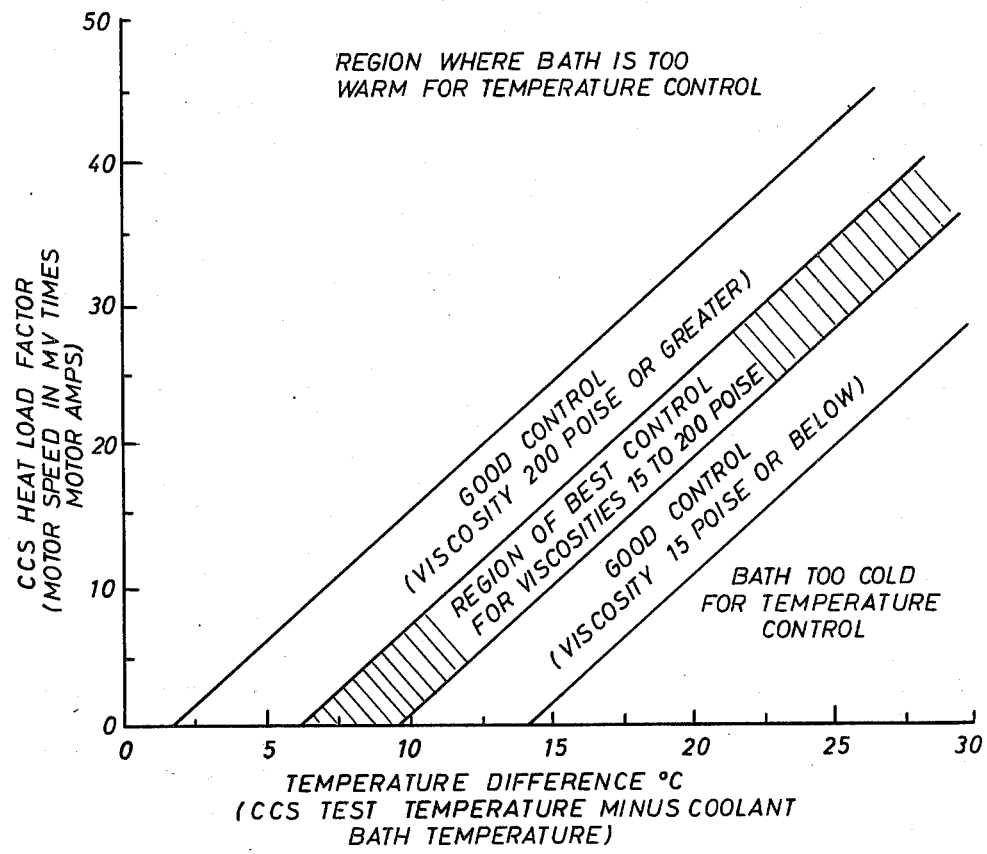
FIG. 4 is a graph illustrating the temperature differential for the cold bath temperature to obtain the best temperature control of the sample to be measured.

Referring to FIG. 4, there is illustrated a graph of a possible temperature differential between the temperature of the coolant fluid in cold bath 90 and the desired temperature for the sample. Plotted as the ordinate scale is the power heating load factor to the sample as a function of the rotor speed, expressed as milivolts out of the tachometer 86, times the motor 80 drive current. The slope of the curves and the separation therebetween are functions of the parameters of particular instruments being used to perform the cooling function. In other words, for different conduit 94, 96 sizes carrying the coolant fluids, different sizes of the passages 94 in the stator 66, etc., the preferred magnitude of the temperature differential between the temperature of the bath 90 and the desired temperature for the measurement will vary. By providing a constant temperature differential for each temperature at which measurements are to be made, a constant heat transfer characteristic for the system can be obtained.

For one possible system which has been shown to work, for lubricating oils whose viscosity is approximately 15 to 200 poise, a temperature differential of approximately 6° to 10° C. provides the best control, with 10° being the preferred value. For viscosities of 200 poise or greater, a temperature differential of 5° C. has been found to work quite well. For viscosities of 15 poise or less, a temperature differential of 13°–14° C. was preferred. In all cases, the temperature differential will be in the range of 5°–20° C.

In operation, the temperature control of the sample to be measured begins by selection of the set point of the temperature of the coolant fluids in cold bath 90. The coolant fluids from bath 90 are then circulated by the circulating means 93 in response to control signals from the microprocessor 62. These cold coolant fluids are circulated via conduits 93, 94 to the stator 66 for circulation therethrough. Because the coolant fluids from cold bath 90 are maintained at a constant predetermined temperature differential below the desired temperature for the sample, the rangeability of the temperature control system is extended. The extended rangeability results because a constant driving force for heat transfer between the sample, i.e., the stator 66, and the coolant fluids are provided for all temperatures. The temperature probe 88 monitors the temperature of the stator 66 and applies its output signal to the microprocessor 62 and to the coolant bath 90 temperature controller (not shown).

Because the temperature probe 88 is not monitoring the temperature of the sample directly, i.e., the temperature probe 88 is not in direct contact with the sample, there is a temperature difference between the temperature of the stator and the temperature of the sample. This difference is compounded by the fact that there will be heating of the sample by rotation of the rotor 74 during an actual viscosity measurement. It is one of the novel features of the present invention that by maintaining the cold bath 90 coolant fluids at a constant temperature differential below the desired temperature for the sample, the present invention is able to obtain a constant repeatable heat transfer characteristic for the system.

In response to the temperature indicated by thermistor 88, the temperature controller, which control the temperature of the coolant bath, control circulating means 93 to apply the coolant fluids to conduits 94, 96. Control of the solenoid valves (not shown) used to apply the fluids into the conduits 94, 96 are on a time proportion basis for a 1 second cycle time. In other words, during every 1 second interval, the valves are opened and closed, with the duty cycle of the on-to-off time controlled by the indicated temperature from thermistor 88. In this way, the temperature of the stator 66 and the sample contained therein are cooled to the desired temperature.

At the conclusion of the viscosity measurement, the measured sample is then heated to a higher temperature to lower the viscosity of the fluid sample to permit the complete and easy removal of the sample from the sample cavity 68 by the sample supply system 14. To accomplish the heating of the stator 66, and the sample contained therein, the circulating means 93 is controlled by the microprocessor 62 to apply the hot coolant fluids from hot bath 91 to the conduits 93, 94 and the stator 66. Because a hot bath 91 of hot coolant fluids is available for immediate application to the stator 66, it is possible to minimize the turnaround time from viscosity measurement to viscosity measurement. There is no need to wait for a heating cycle of any fluids prior to beginning the heating cycle of the measured sample. Hot bath 91 is immediately available for application to the stator 66.

In the preferred embodiment of the present invention, the actual viscosity measurement is obtained by rotation of the rotor 74 within the sample cavity 68 in response to drive signals from microprocessor 62. A programmable DC current source 79 responds to control signal from microprocessor 62 to provide a source of constant DC current to drive motor 80. As previously described, drive motor 80 results in rotation of rotor 74 within the stator 66. Eventually, the rotor 74 will obtain some speed of rotation. The speed of rotation of rotor 74 when the motor 80 is driven with a constant predetermined drive current represents the viscosity of the sample being measured.

During measurement of the viscosity, a quantity of the sample being measured is always maintained in the shear zone between the walls of the sample cavity 68 and the outer surfaces of the rotor 74, even when the viscoelastic effect of the sample causes a quantity of the sample in the sample cavity 68 to spiral up onto the rotor shaft 76 or spill out onto the top of the stator 66. A steady supply of the sample being measured is provided by the sample supply system 14 via conduit 70 during the viscosity measurement. Speed indicator 86 monitors the speed of rotation of the rotor 74 and supplies this measurement to the microprocessor 62 which determines from the speed of rotation the cold cranking viscosity of the sample. In the preferred embodiment, the speed indicator 86 is an incremental optical shaft encoder, although other indicators, such as an analog tachometer, could also be used.

After the purging of the sample capacity of the old sample by the new sample from the automatic supply system 14, the circulating means 93 introduces the cold coolant fluids from the cold bath 90 to the stator 66 for circulation therein. Approximately 180 seconds after the start of the cooling cycle, the viscosity measurement begins. At this point, microprocessor 62 controls the constant DC current source to supply drive signals to the motor 80. A period of approximately 60 seconds is allowed to elapse before a reading of the speed of rotation of the rotor is taken. This permits adequate time for the rotor to achieve its steady state rotational speed.

In an alternate embodiment of the viscometer 12 of the invention, the microprocessor 62 causes the DC current source 79 to supply a drive current to the motor 80. The drive current to motor 80 is controlled to achieve a constant rotor speed. The desired speed of rotation for the rotor 74 is monitored by the microprocessor 62 from the speed indicator 86. During rotation of the rotor 74, a device 81 connected to the housing of the motor 80 is monitored to determine the amount of torque required to prevent rotation of the housing of motor 80 when the rotor 74 has obtained the desired speed of rotation. The magnitude of the torque required to prevent rotation of the motor 80 represents the viscosity of the sample.

In yet another embodiment, the constant rotor 74 speed could be obtained by using an AC synchronous motor 80 in place of the DC motor to drive the rotor 74 at a constant speed. The AC synchronous motor is then driven by a source of AC drive current. Measurement of the torque required to restrain rotation of the stator of the motor still indicates the viscosity of the sample.

The stator 66 is provided with an annular groove 98 which surrounds the sample cavity 68 for receiving overflow liquid which overflows from the cavity 68 during use. The groove 98 is connected to a waste conduit 99 for leading waste liquid to a dump zone.

In the embodiment illustrated in FIG. 2, an alternative form of locating means is shown to the locating means 28.1 of FIG. 1. In FIG. 2, the locating means comprises a plurality of locating members 28.2 which are mounted on the locating stations 24. Each locating member 28.2 comprises a spring clamp for removably clamping a syringe 26 on its locating station 24.

In use, disposable syringes 26 are filled with the lubricant oils to be tested and are then located on the turntable 18 by means of the locating means 28. The microprocessor 62 may then be set to control rotation of the turntable 18 and thus the order in which the syringes 26 will be brought into register with the discharge member 34 and guide tube 44.

When a selected syringe 26 has been displaced into its registering position by the turntable 18, the controller 62 will actuate the displacement member 50 to engage the guide inlet 46 with the discharge outlet 30 of that positioned syringe 26.

Thereafter microprocessor 62 will operate the discharge member 34 to cause the screw assembly 38 to be rotated by the stepping motor 42 to advance the discharge arm 40 into engagement with the plunger 32 of that syringe 26.

After heating of the measured sample by the hot coolant fluids from hot bath 91, microprocessor 62 causes the motor 42 to advance the discharge arm 40 at a predetermined high speed to discharge a sample of the liquid contained in that syringe 26 into the guide tube 44 and through to the sample cavity 68 to fill the cavity 68.

The microprocessor 62 will then stop further advance of the discharge arm 40, will open the first and second three-way valves 60.1 and 60.2, and will actuate the purging means 52 to purge that first sample from the sample cavity 68 and from the the guide tube 44.

Thereafter the microprocessor 62 will reset both the first and second three-way valves 60 into their positions where they permit flow through the guide tube 44, and will again actuate the motor 42 to again rapidly advance the discharge arm 40 for discharging a second purging sample of material through the guide tube 44 and into the cavity 68. Thereafter, microprocessor 62 will again control the three-way valves to purge that sample from the system thereby cleaning the system and removing a significant proportion of the remains of previous samples tested in the system.

Thereafter, microprocessor 62 will again rapidly advance the discharge arm 40 to discharge a third sample through the guide tube 44 into the cavity 68. This will be sample which is used for determining the viscosity thereof in the viscosity 12. The cooling cycle will now begin by controlling circulation means 93 to supply cold bath 90 cooling fluids to the stator 66.

Once the viscosity of that sample has been determined at the desired temperature in accordance with either the above described means, such as by driving the rotor 74, determining the rate of rotation of the rotor and recording that rate to indicate the viscosity of the liquid, the microprocessor 62 will again operate the purging system to purge the sample from the cavity 68 and from the guide tube 44.

Thereafter, the microprocessor 62 will control the magazine motor 22 to rotate the turntable 18 and bring a succeeding syringe 26 into register with the guide tube 44 and the discharge member 34.

Because certain motor oils contain polymers which undergo phase changes at low temperatures, certain viscoelastic samples tend to spiral towards the rotor shaft 76 when the rotor 74 is being rotatably driven. This viscoelastic effect causes the sample to climb from the shear zone in the cavity 68 thereby resulting in a lesser charge of sample in the cavity 68. This diminished volume of sample in the cavity 68 as a result of such loss of sample will cause the rotor speed to increase thereby giving a false indication of the apparent viscosity of the sample.

For such motor oils or lubricants which exhibit a viscoelastic effect, microprocessor 62 is programmed to drive the discharge member 34 at a slow rate after the sample to be tested has been discharged through the guide tube into the cavity 68.

The discharge arm 40 will therefore be advanced at a slow rate to continue to supply lubricating oil from the same syringe 26 through the guide tube 44 and into the cavity 68 to replace the lubricating oil which is drawn out of the cavity 68 as a result of the viscoelastic effect. This will therefore balance the volume of fluid being tested in the cavity 68 so that the rotor speed will give a sufficiently accurate indication of the viscosity of the sample. The overflow of lubricating fluid from the cavity 68 as a result of the viscoelastic effect, will flow into an annular groove 98 provided around the cavity 68. The overflow into the annular groove 98 will flow away through a discharge trough 99.

To aid in controlling the supply of compensating lubricating oil to compensate for oil loss through the viscoelastic effect, the system 10 includes a sensor 100 and a light source 102. The sensor 100 is electrically connected to the controller 62 so that the sensor 100 may sense the extent of the viscoelastic effect and the controller 62 may thus control the rate at which the liquid is supplied by the discharge member 34 to compensate for the liquid loss in the cavity 68 from the viscoelastic effect.

By controlling operation of the discharge member 34 so that the first, or first and second purging samples, and the sample to be tested are discharged rapidly, a reduction in the time involved in running each test is achieved. Thereafter the slow discharge to compensate for the viscoelastic effect can be run at a rate to balance the rate of loss of liquid from the cavity 68. The embodiment of the invention as illustrated in the drawings therefore provides the advantage that samples of fluids to be tested can readily be loaded into standard syringes at a location remote from the CCS system 10. These samples can then readily be located in position on the locating stations 24 of the turntable 18 when desired. They can be located in a required order or, if desired, the microprocessor 62 can be programmed to bring the syringes 26 into register with the discharge member 34 in any appropriate order.

The microprocessor 62 can then automatically control all operations of the sample supply system 14 and of the viscometer 12 thereby dispensing with the need for constant supervision and attendance.

The invention provides the further advantage that by incorporating an automatic purging system, and using one or more charges of a succeeding sample to purge the system of the preceding sample, the remnants of the preceding sample can be effectively removed without the use of undesirable cleaning procedures and fluids. In addition, any remnants of a preceding sample remaining after purging, would in any event be more compatible with the sample being tested than would be the case where cleaning fluids of much lower viscosities are employed as in the prior-art procedures.

By using individual syringes which are actuated from outside the receptacles 26, contamination is reduced substantially. This is particularly so when compared to the prior-art systems in which large pump or vacuum systems are employed to dispense the materials to be tested. In these systems the large pump systems, manifold systems or suction systems, which present relatively large surface areas in relation to the volumes of the sample, have to be cleaned. This is therefore much more tedious and substantially increases the possibility of contamination of succeeding samples by precedings samples.

The embodiment as illustrated in the drawings provides the further advantage that a large number of samples can be tested sequentially either in a predetermined or a random order, as may be required.

The embodiment of the invention will therefore save manpower, improve precision by having an accurately controlled temperature of the sample, discharge rate and volume, and by speeding up the rate at which tests can be performed.

While the embodiment as illustrated with reference to the drawings, is a viscometer system 12, it will be appreciated that the sample supply system 14 of this invention can equally be incorporated or used with other instruments and systems which require or use samples of fluent materials which are dispensed periodically. This is particularly the case for instruments or systems which require constant volumes of samples at substantially constant or at several substantially constant rates. It will also be appreciated that the sample supply system can be used with other viscometer system which use methods different than those disclosed above for measuring the cold cranking viscosity of fluent materials.

We claim:

1. A viscometer for measuring the cold temperature viscosity of a fluent sample contained in a sample chamber having means therethrough for receiving fluid coolants separate from the sample, the viscometer comprising:
   (a) a DC current source for providing a constant predetermined DC drive current;
   (b) a rotor member submersed in the fluent sample in said sample chamber, said rotor and said sample chamber defining therebetween a shear zone containing a portion of the sample to be measured;
   (c) a DC motor connected to said rotor member and responsive to the drive current for rotating said rotor member;
   (d) a means for measuring the speed of rotation of said rotor member, the rotor speed representing the viscosity of the sample;
   (e) a coolant bath containing a cooling fluid for cooling the sample to the desired temperature at which the viscosity measurement is to be taken, the temperature of said coolant bath controlled to a constant temperature differential below the desired temperature for the measurement;
   (f) a hot bath containing a heating fluid for heating the sample contained in said sample chamber; and
   (g) a fluid circulating means for selectively circulating either the cooling or heating fluid through the coolant receiving means in said sample chamber whereby,
      (i) circulation of the constant temperature differential cooling fluid controls the temperature of the sample to be measured to the desired temperature for the viscosity measurement, and
      (ii) circulation of the heating fluid heats the measured sample to obtain a lower viscosity to permit the rapid and complete removal of the sample from the sample chamber.

2. The viscometer of claim 1 wherein said means for measuring the speed of rotation of said rotor member comprises a tachometer.

3. The viscometer of claim 1 wherein said means for measuring the speed of rotation of said rotor member comprises an optical incremental shaft encoder.

4. A microprocessor controlled viscometer for measuring the cold cranking viscosity of a sample of lubricating oil contained in a shear zone defined by the space between an outer stationary stator and an inner rotatable rotor, the stator having means therein for receiving fluid coolants separate from the sample, the viscometer comprising:
  (a) a microprocessor programmed to monitor the temperature of each sample and to determine the viscosity of each sample from the speed of rotation of said rotor;
  (b) a rotor drive means responsive to said microprocessor for rotating said rotor;
  (c) a speed indicator responsive to rotation of said rotor, the speed of rotation of said rotor representing the viscosity of the sample;
  (d) a supply of cooling fluid responsive to said microprocessor for cooling the sample contained in said stator to the desired temperature at which the viscosity measurement is to be taken, the temperature of the cooling fluid maintained at a predetermined constant temperature differential below the desired temperature;
  (e) a supply of heating fluid for heating the sample contained in said stator; and
  (f) a circulating means responsive to said microprocessor for selectively circulating the cooling and heating fluids through the coolant receiving means in said stator whereby,
    (i) circulation of the constant temperature cooling fluid lowers the temperature of the sample to be measured to the desired temperature for the viscosity measurement, and
    (ii) circulation of the heating fluid heats the measured sample to obtain a lower viscosity to permit the rapid and complete removal of the sample from the sample chamber.

5. The viscometer of claim 4 wherein said rotor drive means includes:
  (a) a programmable regulated DC current source responsive to said microprocessor for delivering a constant DC current drive signal; and
  (b) a DC motor connected to said rotor and responsive to the DC current drive signal for rotating said rotor and said speed indicator.

6. The viscometer of claims 4 or 5 wherein said means for measuring the rotation of said rotor comprises an incremental shaft encoder.

7. The viscometer of claim 4 further including a temperature sensing probe contained in said stator for indicating the temperature of the sample currently being measured.

8. The viscometer of claim 7 wherein said temperature sensing probe is a thermistor.

9. A viscometer adapted for use in a cold cranking simulator system for measuring the cold cranking viscosity of lubricating oils, the simulator system sequentially measuring the viscosity of a plurality of lubricating oil samples, the viscometer comprising:
  (a) a sample container for receiving a sample to be measured, said container including means separate from the sample for circulating coolant fluids therethrough to control the sample temperature for the viscosity measurement, said container further including a rotatable rotor contained therein and surrounded by the sample to be measured, said rotor and said sample container defining therebetween a shear zone containing a portion of the sample to be measured;
  (b) a drive means connected to said rotor for rotating said rotor within said sample container;
  (c) a measurement means responsive to the rotation of said rotor for measuring the viscosity of the sample;
  (d) a source of cooling fluid for cooling the sample in said sample container to the desired temperature for the viscosity measurement, the temperature of the cooling fluid maintained at predetermined constant temperature differential below the desired temperature for the sample; and
  (e) a means independent of said source of cooling fluid for heating said container and sample after each viscosity measurement to decrease the viscosity of the sample oil to enable the rapid replacement of the old sample with a new sample.

10. The viscometer of claim 9 wherein said drive means includes
  (a) a controllable DC power source for generating a drive signal;
  (b) a motor responsive to the drive signal for rotating said rotor; and
  (c) a speed indicator connected to said rotor for indicating the speed of said motor, said measurement means measuring the viscosity of the sample by,
    (i) controlling said DC power source to deliver a constant predetermined DC current to said motor, and
    (ii) measuring the speed of rotation of said rotor, where the speed represents the viscosity of the sample.

11. The viscometer of claim 9 wherein said drive means includes:
  (a) a controllable DC power source for generating a drive signal;
  (b) a motor responsive to the drive signal for rotating said rotor, said motor having a stator; and
  (c) a speed indicator connected to said rotor for indicating the speed of said motor, said measurement means measuring the viscosity of the sample by,
    (i) controlling said DC power source to deliver current to said motor to obtain a desired speed of rotation of said motor, and
    (ii) measuring the torque required to prevent rotation of said motor stator when the desired motor speed has been obtained, the required torque representing the viscosity of the sample.

12. The viscometer of claim 9 wherein the said drive means includes:
  (a) an AC synchronous motor for rotating said rotor at a constant speed, said motor having a stator; and
  (b) a speed indicator connected to said rotor for indicating the speed of said motor, said measurement means measuring the viscosity of the sample by,
    (i) driving said AC motor to obtain the constant speed of rotation of said motor, and
    (ii) measuring the torque required to prevent rotation of said motor stator when the constant motor speed has been obtained, the required torque representing the viscosity of the sample.

13. The viscometer of claims 9, 10, 11 or 12 wherein said heating means comprises a source of heating fluid independent of said cooling fluid whereby heating of a measured sample prior to removal is accomplished by circulation of the heating fluid through said sample chamber in place of the cooling fluid.

14. A cold cranking simulator for automatically measuring the cold cranking viscosity for each of a plurality of fluent samples, comprising:

(a) a stator having a sample receiving zone for receiving the sample to be measured, said stator further including means separate from the sample for receiving fluid coolants to control the temperature of the sample, and a temperature probe for generating a signal as a function of the temperature of the stator;

(b) a rotatable rotor contained in said stator and in contact with the sample to be measured, said rotor and said stator defining therebetween a shear zone containing a portion of the sample to be measured;

(c) a drive means connected to said rotor, said drive means rotating said rotor without rotation of said stator;

(d) a control means for controlling said drive means to rotate said rotor, the resultant speed of rotation of said rotor representative of the viscosity of the sample;

(e) a source of coolant fluid responsive to said control means, said source containing a hot bath of coolant fluid for heating the sample in said sample receiving zone prior to removal of the measured samples and a cold bath of coolant fluid for cooling the sample to the desired temperature at which the viscosity measurement is to be taken, the temperature of said cold bath controlled to a constant predetermined temperature differential below the desired temperature for the measurement;

(f) a fluid circulating means responsive to said control means for selectively circulating either the cooling or heating fluid through the coolant receiving means in said stator whereby, (i) circulation of the cold bath coolant cooling fluid controls the temperature of the sample to the desired temperature for the viscosity measurements, and (ii) circulation of the hot bath coolant fluid heats the sample to obtain a lower viscosity to permit the rapid and complete removal of the sample from the sample chamber; and (g) a sample supply system responsive to said control means for supplying successive samples of fluent material to the sample receiving zone whereby each sample next to be measured is used to purge the measured sample from the sample receiving zone during loading of the next sample.

15. The simulator of claim 14 wherein said drive means includes:

(a) a controllable DC power source for generating a drive signal;

(b) a motor responsive to the drive signal for rotating said rotor; and (c) a speed indicator connected to said rotor for indicating the speed of said motor, said measurement means measuring the viscosity of the sample by, (i) controlling said DC power source to deliver a constant predetermined DC current to said motor, and (ii) measuring the speed of rotation of said rotor, where the speed represents the viscosity of the sample.

16. The simulator of claim 15 wherein said control means is a microprocessor programmed to automatically control said DC power source to deliver the predetermined drive current to said motor, said microprocessor, (i) responding to the output from said speed indicator to determine from the resulting motor speed the viscosity of the sample, and (ii) responding to the temperature probe signal to control said circulating means to maintain the sample at the desired temperature for the viscosity measurement.

17. The simulator of claim 14 wherein said drive means includes:

(a) a controllable DC power source for generating a drive signal;

(b) a motor responsive to the drive signal for rotating said rotor, said motor having a housing; and (c) a speed indicator connected to said rotor for indicating the speed of said motor, said measurement means measuring the viscosity of the sample by, (i) controlling said DC power source to deliver current to said motor to obtain a desired speed of rotation of said motor, and (ii) measuring the torque required to prevent rotation of said motor stator when the constant motor speed has been obtained, the required torque representing the viscosity of the sample.

18. The simulator of claim 17 wherein said control means is a microprocessor programmed to automatically control said DC power source to deliver drive current to said motor, said microprocessor, (i) responding to the output of said speed indicator to determine when the motor-rotor combination has obtained a desired constant speed, (ii) measuring the amount of torque required to prevent said motor from rotating when the motor-rotor combination is rotating at the desired constant speed, the measured torque representing the viscosity of the sample, and (iii) responding to the temperature probe signal to control said circulating means to maintain the sample at the desired temperature for the viscosity measurement.

19. The simulator of claim 14 wherein said drive means includes:

(a) an AC synchronous motor for rotating said rotor at a constant speed, said motor having a motor stator; and (b) a speed indicator connected to said rotor for indicating the speed of said motor, said measurement means measuring the viscosity of the sample by, (i) driving said AC motor to obtain the constant speed of rotation of said motor, and (ii) measuring the torque required to prevent rotation of said motor stator when the constant motor speed has been obtained, the required torque representing the viscosity of the sample.

20. The simulator of claims 14, 16 or 18 wherein said sample supply system comprises:

(a) a magazine having a plurality of locating stations for locating sample receptacles on the magazine, said sample receiving zone receiving samples of fluent material discharged from such sample receptacles; and (b) a discharge member adapted to be actuated to withdraw fluent material from a sample receptacle, the magazine being displaceable relatively to the sample receiving zone and the discharge member to bring any locating station into register with the sample receiving zone and the discharge member for the discharge of fluent material from a receptacle located at such locating station.

21. The simulator according to claim 20, in which the discharge member comprises a discharge arm which is adapted to be displaced relatively to a locating station to apply pressure to a fluent material in a receptacle located at such station.

22. The simulator according to claim 21, in which the discharge arm is adapted to be displaced to displace a displaceable wall associated with a fluent material receptacle located on a locating station.

23. The simulator according to claim 22, in which the discharge member includes a screw assembly to which the discharge arm is connected, with the screw assembly being adapted to be rotatably driven to advance and retract the discharge arm.

24. The simulator according to claim 23, including a motor for driving the screw assembly.

25. The simulator according to claim 23, including a controller for controlling operation of the screw motor, the controller being programmed to drive the screw assembly to discharge a first purging sample from a receptacle and then to discharge a first handling sample to be handled from the same receptacle.

26. The simulator according to claim 23, in which the controller is programmed to drive the screw assembly to discharge a first purging sample of a fluent material at a high speed, then to discharge a first handling sample of the same material at a high speed, and then to continue the discharge of the same fluent material at a low speed for compensating for fluent material loss resulting from a viscoelastic effect.

27. A system according to claim 26, in which the clamps are spring clamps which are mounted at the locating stations, and which are shaped to clamp syringe type receptacles at the locating stations.

28. The simulator according to claim 26, in which the locating means comprises an annular locating ring having a plurality of circumferentially spaced downwardly directed recesses for receiving sample receptacles to thereby locate such receptacles at the locating stations when the ring is positioned on the turntable.

29. The simulator according to claim 21, in which the discharge member includes a screw assembly to which the discharge arm is connected, with the screw assembly being adapted to be rotatably driven to advance and retract the discharge arm.

30. The simulator according to claim 29, including a motor for driving the screw assembly.

31. The simulator according to claim 30, including a controller for controlling operation of the screw motor, the controller being programmed to drive the screw assembly to discharge a first purging sample from a receptacle and then to discharge a first handling sample to be handled from the same receptacle.

32. The simulator according to claim 31, in which the controller is programmed to drive the screw assembly to discharge a first purging sample of a fluent material at a high speed, then to discharge a first handling sample of the same material at a high speed, and then to continue the discharge of the same fluent material at a low speed for compensating for fluent material loss resulting from a viscoelastic effect.

33. The simulator according to claim 20, in which the magazine comprises a rotatable member which is adapted to be rotatably driven to position the locating stations selectively in register with the discharge member and the sample receiving zone.

34. The simulator according to claim 33, in which the rotatable member comprises an annular turntable having circumferentially spaced locating stations and having locating means for locating receptacles on the spaced locating stations.

35. The simulator according to claim 34, in which the locating means comprises slots provided at the locating stations for receiving flanges extending from sample receptacles to locate such receptacles on the locating stations.

36. The simulator according to claim 35, in which the locating means comprises locating members in the form of clamps for removably clamping receptacles at the locating stations.

37. The simulator according to claims 34, in which the locating means comprises locating members in the form of clamps for removably clamping receptacles at the locating stations.

38. A system according to claim 37, in which the clamps are spring clamps which are mounted at the locating stations, and which are shaped to clamp syringe type receptacles at the locating stations.

39. The simulator according to claims 34, in which the locating means comprises an annular locating ring having a plurality of circumferentially spaced downwardly directed recesses for receiving sample receptacles to thereby locate such receptacles at the locating stations when the ring is positioned on the turntable.

40. The simulator according to claim 33, including a motor for driving the rotatable member, said rotatable member motor responsive to said control means for controlling operation of the rotatable member motor to bring the locating stations successively into register with the discharge member in a predetermined order.

41. The simulator according to claim 20, in which the sample receiving zone includes a guide tube to guide discharged fluent material to said stator.

42. The simulator according to claim 41, in which the guide tube has a guide inlet at one end and a guide outlet at its other end, and in which the guide tube is displaceable between an operative position where its guide inlet can register with a discharge outlet of a receptacle located at a registering locating station and an inoperative position where its guide inlet would be spaced from such a receptacle discharge outlet.

43. The simulator according to claim 42, in which the guide tube has a purging section intermediate its ends, and in which the system includes purging means for purging the guide tube of fluent material between successive discharges of fluent materials.

44. The simulator according to claim 42, in which the purging means comprises a first purging conduit extending from the purging section for connection to a suction source, and a first valve between the purging section and the first purging conduit, the first valve being operable to selectively purge the guide tube.

45. The simulator according to claim 42, including a displacement member for displacing the guide tube between its operative and inoperative positions.

46. The simulator according to claim 45, in which the guide tube has a purging section intermediate its ends, and in which the system includes purging means for purging the guide tube of fluent material between successive discharges of fluent materials.

47. The simulator according to claim 45, in which the purging means comprises a first purging conduit extending from the purging section for connection to a suction source, and a first valve between the purging section and the first purging conduit, the first valve being operable to selectively purge the guide tube.

48. The simulator according to claims 41, in which the guide tube has a purging section intermediate its ends, and in which the system includes purging means for purging the guide tube of fluent material between successive discharges of fluent materials.

49. The simulator according to claim 48, in which the purging means comprises a first purging conduit extending from the purging section for connection to a suction source, and a first valve between the purging section and the first purging conduit, the first valve being operable to selectively purge the guide tube.

50. The simulator according to claim 49, in which the purging means further comprises a second purging conduit and a second valve, in which the second purging conduit extends from the purging section proximate one end of the guide tube, in which the first purging conduit extends from the purging section proximate an opposed end of the guide tube, and in which the first and second valves are selectively operable to purge selected parts of the guide tube.

51. The simulator of claim 50 wherein said speed indicator is an optical incremental shaft encoder.

52. The simulator of claim 20 wherein said speed indicator is an optical incremental shaft encoder.

* * * * *